United States Patent
Yoshikawa et al.

(10) Patent No.: US 10,585,087 B2
(45) Date of Patent: Mar. 10, 2020

(54) METHOD FOR EVALUATING AND SELECTING AGENT FOR SUPPRESSING ODORS OF SULFIDE COMPOUNDS

(71) Applicant: KAO CORPORATION, Tokyo (JP)

(72) Inventors: Keiichi Yoshikawa, Omiya-Ku (JP); Naoko Saito, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 35 days.

(21) Appl. No.: 15/737,079

(22) PCT Filed: Jun. 16, 2016

(86) PCT No.: PCT/JP2016/067894
§ 371 (c)(1),
(2) Date: Dec. 15, 2017

(87) PCT Pub. No.: WO2016/204211
PCT Pub. Date: Dec. 22, 2016

(65) Prior Publication Data
US 2018/0180600 A1 Jun. 28, 2018

(30) Foreign Application Priority Data

Jun. 17, 2015 (JP) ................. 2015-121916
Jun. 10, 2016 (JP) ................. 2016-116227

(51) Int. Cl.
| | |
|---|---|
| G01N 33/53 | (2006.01) |
| G01N 33/566 | (2006.01) |
| C07K 14/705 | (2006.01) |
| C12Q 1/06 | (2006.01) |
| G01N 33/50 | (2006.01) |

(52) U.S. Cl.
CPC .............. *G01N 33/53* (2013.01); *C12Q 1/06* (2013.01); *G01N 33/5038* (2013.01); *G01N 33/566* (2013.01); *F01N 2560/027* (2013.01)

(58) Field of Classification Search
None
See application file for complete search history.

(56) References Cited

U.S. PATENT DOCUMENTS

| 8,637,259 B1 | 1/2014 | Chatelain et al. |
| 2013/0216492 A1 | 8/2013 | Kato et al. |
| 2013/0336910 A1 | 12/2013 | Chatelain et al. |
| 2014/0186864 A1 | 7/2014 | Kato et al. |

FOREIGN PATENT DOCUMENTS

| JP | 2004-504010 A | 2/2004 |
| JP | 2006-206882 A | 8/2006 |
| JP | 2010-4971 A | 1/2010 |
| JP | 2012-50411 A | 3/2012 |
| JP | 2012-249614 A | 12/2012 |
| JP | 2015-211667 A | 11/2015 |
| WO | 01/68805 A2 | 9/2001 |
| WO | 2006/094704 A2 | 9/2006 |
| WO | WO 2012/169644 A1 | 12/2012 |
| WO | 2014/210585 A2 | 12/2014 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Extended European Search Report dated Nov. 14, 2018 in Patent Application No. 16811685.3.
Eric Block, et al., "Smelling Sulfur: Discovery of a Sulfur-Sensing Olfactory Receptor that Requires Copper", ACS Symposium Series, XP055516849, vol. 1152, 2013, pp. 1-14.
Xufang Duan, et al., "Crucial role of copper in detection of metal-coordinating odorants", Proceedings of the National Academy of Sciences of the United States of America, vol. 109, No. 9, XP055355734, Feb. 28, 2012, pp. 3492-3497.
International Search Report dated Jul. 26, 2016 in PCT/JP2016/067894 filed Jun. 16, 2016.
"*Homo sapiens* olfactory receptor family 4 subfamily S member 2 (OR4S2), mRNA", Database GenBank, , Jul. 2008, NCBI Reference Sequence NM_001004059.2.

* cited by examiner

*Primary Examiner* — Christine J Saoud
*Assistant Examiner* — Jon M Lockard
(74) *Attorney, Agent, or Firm* — Oblon, McClelland, Maier & Neustadt, L.L.P.

(57) ABSTRACT

The present invention identifies substances which suppress odors of sulfide compounds. Provided is a method for evaluating and/or selecting an agent for suppressing odors of sulfide compounds, the method comprising: adding a test substance and a sulfide compound to at least one olfactory receptor polypeptide selected from the group consisting of OR4S2 and polypeptides having an amino acid sequence identity of at least 80% to OR4S2; and measuring the response of the olfactory receptor polypeptide to the sulfide compound.

8 Claims, 4 Drawing Sheets
Specification includes a Sequence Listing.

[Figure 1]
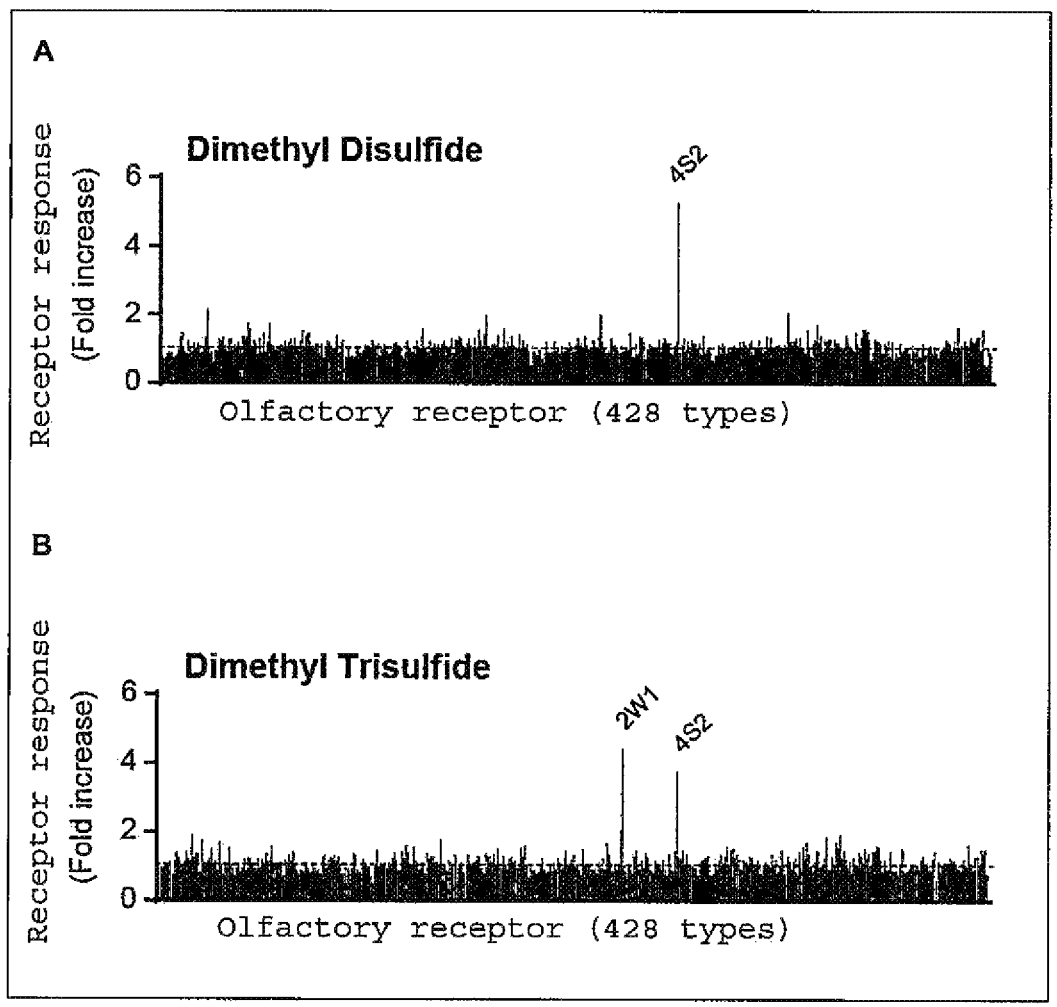

[Figure 2]
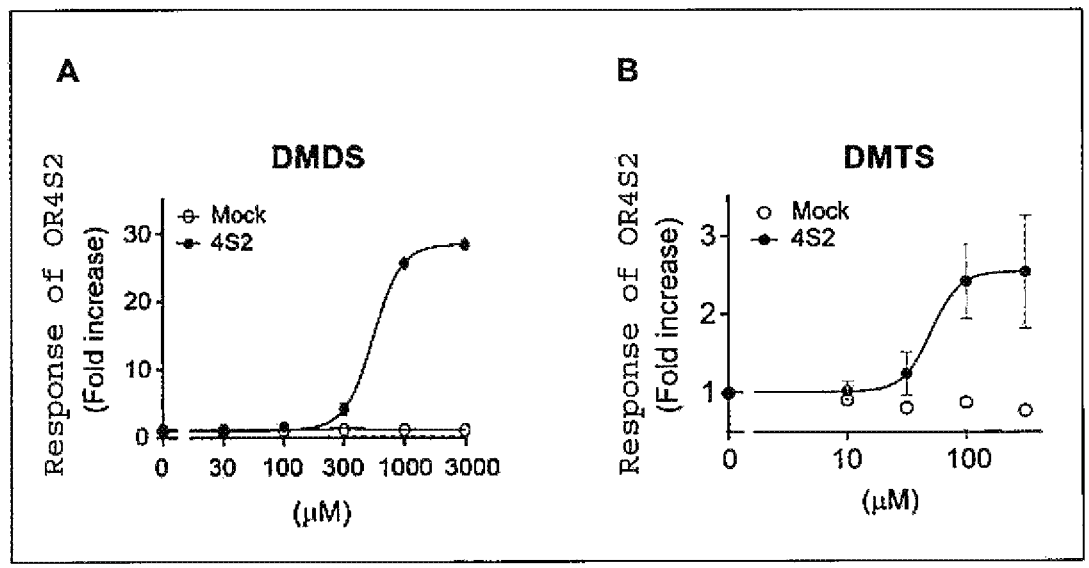
[Figure 3]
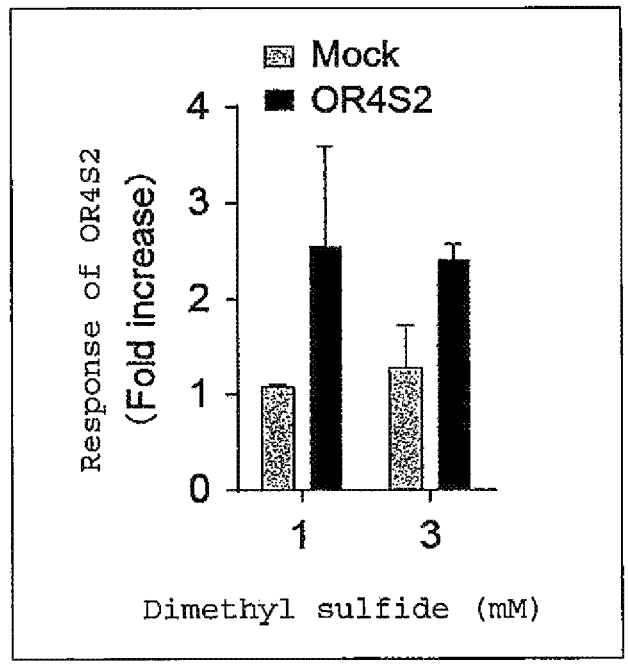

[Figure 4]
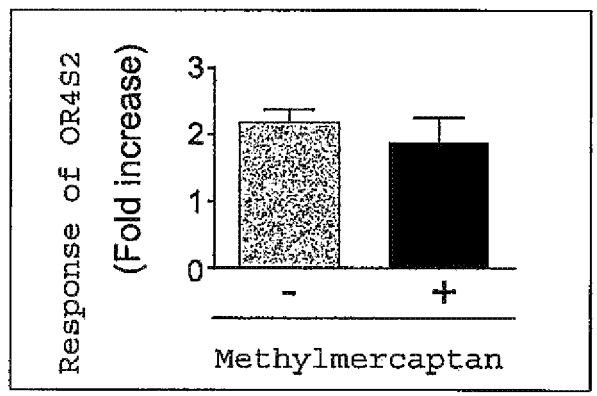
[Figure 5]
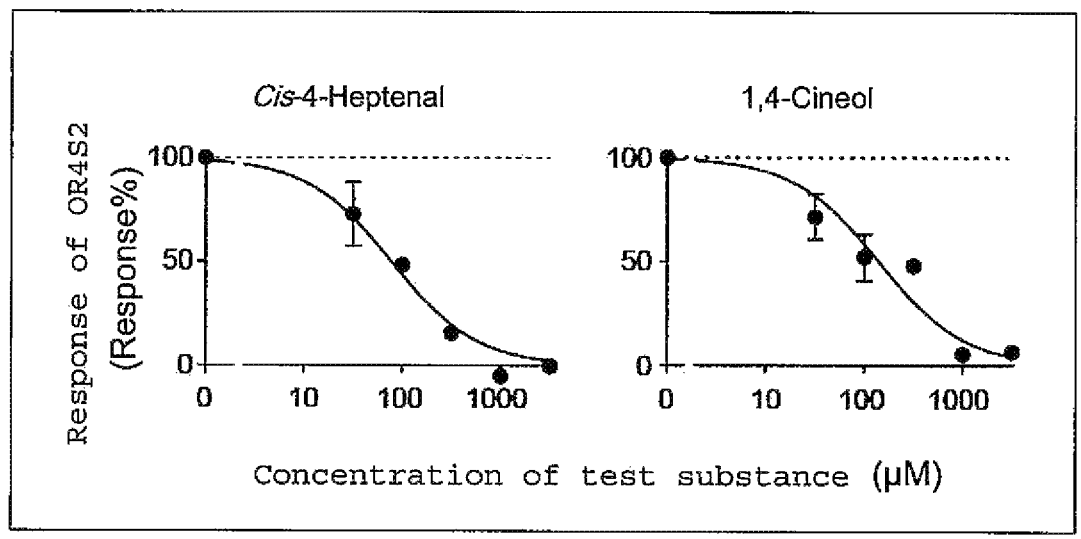

[Figure 6]
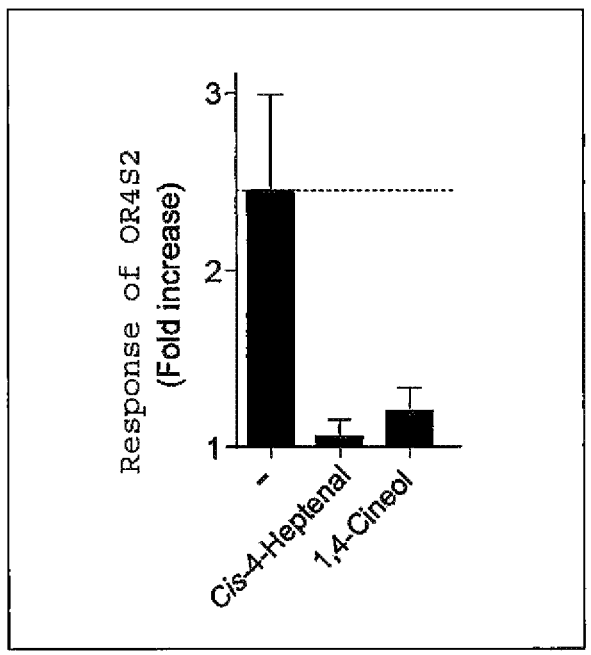
[Figure 7]
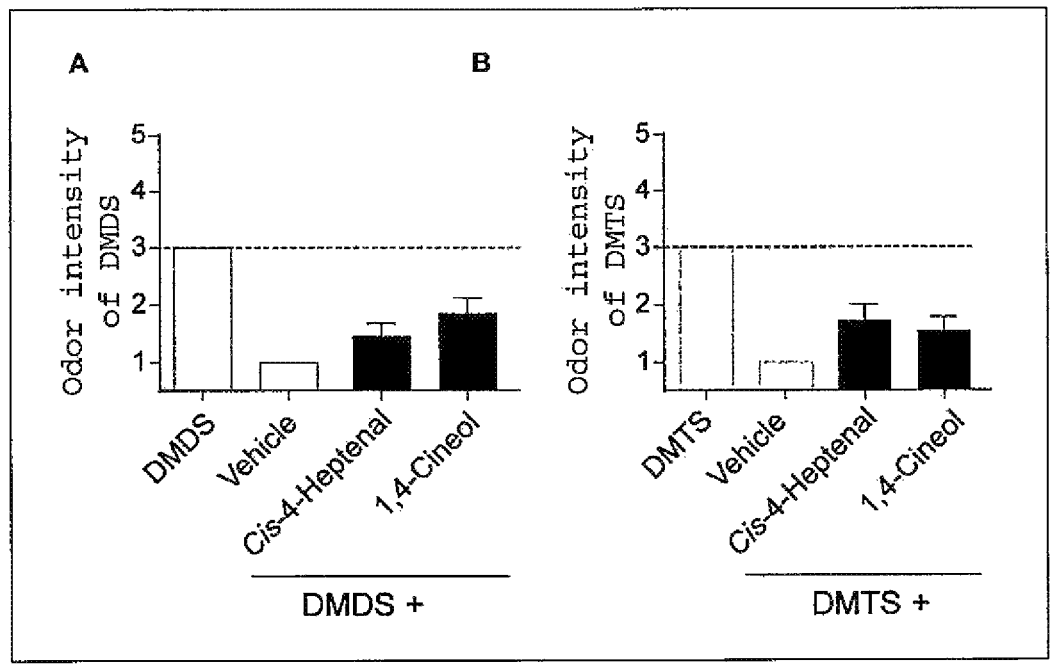

US 10,585,087 B2

SEQUENCE LISTING

<160> NUMBER OF SEQ ID NOS: 4

<210> SEQ ID NO 1
<211> LENGTH: 936
<212> TYPE: DNA

<213> ORGANISM: Homo sapiens
<220> FEATURE:
<223> OTHER INFORMATION: DNA encoding human OR4S2

<400> SEQUENCE: 1

```
atggaaaaaa taaacaacgt aactgaattc attttctggg gtctttctca gagcccagag      60
attgagaaag tttgttttgt ggtgttttct ttcttctaca taatcattct tctgggaaat     120
ctcctcatca tgctgacagt ttgcctgagc aacctgttta agtcacccat gtatttcttt     180
ctcagcttct tgtcttttgt ggacattgt tactcttcag tcacagctcc caagatgatt     240
gttgacctgt tagcaaagga caaaaccatc tcctatgtgg ggtgcatgtt gcaactgttt     300
ggagtacatt tctttggttg cactgagatc ttcatcctta ctgtaatggc ctatgatcgt     360
tatgtggcta tctgtaaacc cctacattat atgaccatca tgaaccggga gacatgcaat     420
aaaatgttat tagggacgtg ggtaggtggg ttcttacact ccattatcca agtggctctg     480
gtagtccaac tacccttttg tggacccaat gagatagatc actacttttg tgatgttcac     540
cctgtgttga aacttgcctg cacagaaaca tacattgttg tgttgttgt gacagccaac     600
agtggtacca ttgctctggg gagttttgtt atcttgctaa tctcctacag catcatccta     660
gtttccctga gaaagcagtc agcagaaggc aggcgcaaag ccctctccac ctgtggctcc     720
cacattgcca tggtcgttat ctttttcggc ccctgtactt ttatgtacat gcgccctgat     780
acgaccttt cagaggataa gatggtggct gtattttaca ccattatcac tcccatgtta     840
aatcctctga tttatacact gagaaatgca gaagtaaaga tgcaatgaa gaaactgtgg     900
ggcagaaatg ttttcttgga ggctaaaggg aaatag                               936
```

<210> SEQ ID NO 2
<211> LENGTH: 311
<212> TYPE: PRT
<213> ORGANISM: Homo sapiens
<220> FEATURE:
<223> OTHER INFORMATION: Human OR4S2

<400> SEQUENCE: 2

```
Met Glu Lys Ile Asn Asn Val Thr Glu Phe Ile Phe Trp Gly Leu Ser
1               5                   10                  15

Gln Ser Pro Glu Ile Glu Lys Val Cys Phe Val Val Ser Phe Phe
            20                  25                  30

Tyr Ile Ile Ile Leu Leu Gly Asn Leu Leu Ile Met Leu Thr Val Cys
                35                  40                  45

Leu Ser Asn Leu Phe Lys Ser Pro Met Tyr Phe Phe Leu Ser Phe Leu
    50                  55                  60

Ser Phe Val Asp Ile Cys Tyr Ser Ser Val Thr Ala Pro Lys Met Ile
65                  70                  75                  80

Val Asp Leu Leu Ala Lys Asp Lys Thr Ile Ser Tyr Val Gly Cys Met
                85                  90                  95

Leu Gln Leu Phe Gly Val His Phe Phe Gly Cys Thr Glu Ile Phe Ile
            100                 105                 110

Leu Thr Val Met Ala Tyr Asp Arg Tyr Val Ala Ile Cys Lys Pro Leu
        115                 120                 125

His Tyr Met Thr Ile Met Asn Arg Glu Thr Cys Asn Lys Met Leu Leu
    130                 135                 140

Gly Thr Trp Val Gly Gly Phe Leu His Ser Ile Ile Gln Val Ala Leu
145                 150                 155                 160

Val Val Gln Leu Pro Phe Cys Gly Pro Asn Glu Ile Asp His Tyr Phe
```

```
                165                 170                 175
        Cys Asp Val His Pro Val Leu Lys Leu Ala Cys Thr Glu Thr Tyr Ile
                    180                 185                 190

Val Gly Val Val Thr Ala Asn Ser Gly Thr Ile Ala Leu Gly Ser
                    195                 200                 205

Phe Val Ile Leu Leu Ile Ser Tyr Ser Ile Ile Leu Val Ser Leu Arg
            210                 215                 220

Lys Gln Ser Ala Glu Gly Arg Arg Lys Ala Leu Ser Thr Cys Gly Ser
        225                 230                 235                 240

His Ile Ala Met Val Val Ile Phe Phe Gly Pro Cys Thr Phe Met Tyr
                        245                 250                 255

Met Arg Pro Asp Thr Thr Phe Ser Glu Asp Lys Met Val Ala Val Phe
                    260                 265                 270

Tyr Thr Ile Ile Thr Pro Met Leu Asn Pro Leu Ile Tyr Thr Leu Arg
                        275                 280                 285

Asn Ala Glu Val Lys Asn Ala Met Lys Lys Leu Trp Gly Arg Asn Val
                290                 295                 300

Phe Leu Glu Ala Lys Gly Lys
        305                 310

<210> SEQ ID NO 3
<211> LENGTH: 681
<212> TYPE: DNA
<213> ORGANISM: Homo sapiens
<220> FEATURE:
<223> OTHER INFORMATION: DNA encoding human RTP1S

<400> SEQUENCE: 3
atgtgtaaaa gcctgaccac aggcgagtgg aagaaaatct tctatgagaa gatggaggag        60
gtgaagccgg ctgacagctg ggacctcatc atggacccca acctccagca caatgtgctg       120
gcccctggtt ggaagcagta cctggaacag catgcttcag caggttccac ctgctcctgg       180
tgctggcaca gctggcagtc gagccagctg gtcatcctct ccacatgta cctggacaag        240 acccagcgga ccggctgcgt gcgcatgcgc gtcttcaagc agctgtgcta tgagtgcggc       300
agcagccggc tggacgagtc cagcatgctg aggagaaaca tcgagggcct ggtggacaac       360
ctcgtgtgca gcctgcgcga gcagtgctac ggcgagaacg gcggccagta ccgcatccac       420
gtggccagcc gccaggacca ccagcggcac cgcgagagt tctgcgaggc ctgccgcctg        480
ggcatcaccc actggaagcc caccgagaag atgctggagg aggaggcgag cacctacacc       540
ttctcccggc ccgcgaaccc cagcaagacc gcggacagcg gcttcagctg cgacttctgc       600
tctctgccct ggtgcatgtt ttgggccacg gtcctgctgc tgatcatcta cctgcagatc       660
tctttcggca accccgtata a                                                 681

<210> SEQ ID NO 4
<211> LENGTH: 226
<212> TYPE: PRT
<213> ORGANISM: Homo sapiens
<220> FEATURE:
<223> OTHER INFORMATION: Human RTP1S

<400> SEQUENCE: 4

Met Cys Lys Ser Leu Thr Thr Gly Glu Trp Lys Lys Ile Phe Tyr Glu
1               5                   10                  15

Lys Met Glu Glu Val Lys Pro Ala Asp Ser Trp Asp Leu Ile Met Asp
                20                  25                  30
```

```
Pro Asn Leu Gln His Asn Val Leu Ala Pro Gly Trp Lys Gln Tyr Leu
        35                  40                  45
Glu Gln His Ala Ser Gly Arg Phe His Cys Ser Trp Cys Trp His Ser
    50                  55                  60
Trp Gln Ser Ser Gln Leu Val Ile Leu Phe His Met Tyr Leu Asp Lys
65                  70                  75                  80
Thr Gln Arg Thr Gly Cys Val Arg Met Arg Val Phe Lys Gln Leu Cys
                85                  90                  95
Tyr Glu Cys Gly Ser Ser Arg Leu Asp Glu Ser Ser Met Leu Glu Glu
            100                 105                 110
Asn Ile Glu Gly Leu Val Asp Asn Leu Val Cys Ser Leu Arg Glu Gln
            115                 120                 125
Cys Tyr Gly Glu Asn Gly Gly Gln Tyr Arg Ile His Val Ala Ser Arg
    130                 135                 140
Gln Asp His Gln Arg His Arg Gly Glu Phe Cys Glu Ala Cys Arg Leu
145                 150                 155                 160
Gly Ile Thr His Trp Lys Pro Thr Glu Lys Met Leu Glu Glu Glu Ala
                165                 170                 175
Ser Thr Tyr Thr Phe Ser Arg Pro Ala Asn Pro Ser Lys Thr Ala Asp
            180                 185                 190
Ser Gly Phe Ser Cys Asp Phe Cys Ser Leu Pro Trp Cys Met Phe Trp
        195                 200                 205
Ala Thr Val Leu Leu Leu Ile Ile Tyr Leu Gln Ile Ser Phe Gly Asn
    210                 215                 220
Pro Val
225
```

METHOD FOR EVALUATING AND SELECTING AGENT FOR SUPPRESSING ODORS OF SULFIDE COMPOUNDS

FIELD OF THE INVENTION

The present invention relates to a method for evaluating or selecting an agent for suppressing odors of sulfide compounds.

BACKGROUND OF THE INVENTION

Volatile sulfur compounds, which are generated from drain outlets or waste such as kitchen garbage, are malodorous components which give unpleasant feelings to people even at low concentration. These volatile sulfur compounds are generated through decomposition of a sulfur-containing amino acid such as cysteine and methionine or a protein containing it in sewage, waste, or the like by the action of a metabolizing enzyme such as methionine lyase and cysteine lyase possessed by bacteria. Among volatile sulfur compounds responsible for unpleasant odors, for example, methylmercaptan is formed from methionine by the action of methionine lyase, and hydrogen sulfide is formed from cysteine by the action of cysteine lyase. Further, from methylmercaptan or hydrogen sulfide, sulfide compounds including dimethyl sulfide, dimethyl disulfide, and dimethyl trisulfide are enzymatically or oxidatively formed, and they are also responsible for malodors.

Patent Literature 1 discloses addition of a fragrance component as a deodorizer or an aromatic agent to a composition for washing, sterilization, anti-staining, or deodorization for drain outlets or the like. Patent Literature 2 discloses that a particular fragrance component inhibits the action of an enzyme to form methylmercaptan from methionine or an enzyme to form hydrogen sulfide from cysteine to suppress malodors caused by volatile sulfur compounds generated from waste, drain outlets, etc.

Mammals including humans recognize a smell through the mechanism in which a smell molecule binds to an olfactory receptor (OR) on an olfactory sensory neuron present in the olfactory epithelium in the upper part of the nasal cavity, and the response of the receptor thereto is transmitted to the central nerve system. For humans, it has been reported that approximately 400 olfactory receptors are present, and genes encoding them account for approximately 2% of the total genes of a human. In general, olfactory receptors and smell molecules are associated in many-to-many relationship. That is, an individual olfactory receptor receives a plurality of structurally similar smell molecules at different affinities, and an individual smell molecule is received by a plurality of olfactory receptors. In addition, it has been reported that a smell molecule which activates an olfactory receptor functions as an antagonist to inhibit the activation of another olfactory receptor. Combination of the responses of a plurality of olfactory receptors provides recognition of an individual smell.

Accordingly, the receptor response to one smell molecule may be inhibited by another smell molecule concomitantly present, which ultimately results in that a completely different smell is recognized. This mechanism is called olfactory receptor antagonism. In contrast to deodorization by addition of another smell of a perfume, an aromatic agent, or the like, the suppression of a smell through the receptor antagonism can specifically disable recognition of a particular malodor, and has an advantage that unpleasant feelings due to a smell of an aromatic agent are not caused.

On the basis of the concept of the olfactory receptor antagonism, several methods for identifying malodor-suppressing substances by using the activity of an olfactory receptor as an indicator have been previously disclosed. For example, Patent Literatures 3 and 4 disclose searching for substances which suppress malodors of hexanoic acid, skatole, etc., by using, as an indicator, the activity of an olfactory receptor specifically responsive to the malodor substances. Patent Literature 5 discloses searching for substances which suppress sweat odor by using, as an indicator, the activity of an olfactory receptor responsive to a particular carboxylic acid(s). Patent Literature 6 discloses a method of identifying agents capable of regulating the function of a polypeptide encoding an olfactory receptor through measurement of the activity of the polypeptide in the presence of isovaleric acid or an equivalent thereof. Patent Literature 7 discloses a method of screening a library of chemical substances for compounds relating to sense of smell through identification of compounds which specifically bind to a polypeptide encoding an olfactory receptor.

However, a technique to suppress malodors of the above-mentioned volatile sulfur compounds generated from waste, drain outlets, or the like on the basis of the olfactory receptor antagonism has not been reported yet.

Patent Literature 1: JP-A-2006-206882
Patent Literature 2: JP-A-2010-004971
Patent Literature 3: JP-A-2012-050411
Patent Literature 4: JP-A-2012-249614
Patent Literature 5: US 2013/0336910 A1
Patent Literature 6: WO 2006/094704
Patent Literature 7: JP-A-2004-504010

SUMMARY OF THE INVENTION

In one aspect, the present invention provides a method for evaluating and/or selecting an agent for suppressing odors of sulfide compounds, the method comprising:

adding a test substance and a sulfide compound to at least one olfactory receptor polypeptide selected from the group consisting of OR4S2 and polypeptides having an amino acid sequence identity of at least 80% to OR4S2; and measuring the response of the olfactory receptor polypeptide to the sulfide compound.

BRIEF DESCRIPTION OF THE DRAWINGS

FIG. 1 shows the response of olfactory receptors to each sulfide compound. The horizontal axis represents individual olfactory receptors, and the vertical axis represents the intensity of response. The data are each an average value from three independent experiments. A: response to dimethyl disulfide, B: response to dimethyl trisulfide.

FIG. 2 shows the response of the olfactory receptor OR4S2 to sulfide compounds at different concentrations. A: response to dimethyl disulfide (DMDS), B: response to dimethyl trisulfide (DMTS). For each of the data, n=3, error bar=±SE.

FIG. 3 shows the response of OR4S2 to dimethyl sulfide. For each of the data, n=3, error bar=SD.

FIG. 4 shows the response of OR4S2 to methylmercaptan. +: with test substance (3 mM), −: without test substance. n=3, error bar=SD.

FIG. 5 shows the effect of suppressing the response of the olfactory receptor OR4S2 to dimethyl disulfide (DMDS) with different test substances. The horizontal axis represents the concentration of a test substance, and the vertical axis represents the response (Response %) of OR4S2 to DMDS. n=3, error bar=±SE.

FIG. 6 shows the effect of suppressing the response of the olfactory receptor OR4S2 to dimethyl trisulfide (DMTS) with different test substances. The vertical axis represents the response (Fold increase) of OR4S2 to DMTS in the presence of a test substance. –: without test substance. n=3, error bar=SE.

FIG. 7 shows results of sensory evaluation for the malodor-suppressing effect of test substances. A: odor-suppressing effect for dimethyl disulfide (DMDS), B: odor-suppressing effect for dimethyl trisulfide (DMTS). DMDS=single DMDS, DMTS=single DMTS, Vehicle=single mineral oil, n=10 for DMDS, n=11 for DMTS, error bar=SE.

DETAILED DESCRIPTION OF THE INVENTION

Various volatile sulfur compounds are generated from drain outlets or waste such as kitchen garbage in association with rot caused by bacteria, and cause malodors. One of main causal substances for such malodors is a sulfide compound such as dimethyl sulfide, dimethyl disulfide, and dimethyl trisulfide. Thus, control of odors of these sulfide compounds is required.

The present inventors succeeded in newly identifying an olfactory receptor specifically responsive to sulfide compounds as causal substances for malodors from drain outlets or waste such as kitchen garbage. In addition, the present inventors found that substances capable of suppressing odors of sulfide compounds through the olfactory receptor antagonism can be evaluated and/or selected by using the response of the olfactory receptor or a polypeptide having a function comparable to the olfactory receptor as an indicator.

The present invention enables searching for substances capable of selectively deodorizing odors of sulfide compounds through the olfactory receptor antagonism in an efficient manner.

In the present specification, the term "suppression of odor through the olfactory receptor antagonism" refers to a means in which an odor molecule of interest and an additional molecule are applied together to allow the additional molecule to inhibit the receptor response to the odor molecule of interest and eventually suppress odor recognized by an individual. Suppression of odor through the olfactory receptor antagonism is discriminated from a means in which odor of interest is hidden with an aromatic smell of a fragrance as deodorization with an aromatic agent, although the means is similar in that an additional molecule is used. One example of suppression of odor through the olfactory receptor antagonism is use of a substance inhibitory to the response of an olfactory receptor such as an antagonist (antagonistic agent). To a receptor for an odor molecule causing a particular odor, a substance inhibitory to the response of the receptor to the odor molecule is applied, and then the response of the receptor to the odor molecule is suppressed, and thus odor perceived by an individual can be ultimately suppressed.

In the present specification, the term "olfactory receptor polypeptide" refers to an olfactory receptor or a polypeptide having a function comparable to an olfactory receptor, and the polypeptide having a function comparable to an olfactory receptor refers to a polypeptide which can be expressed on the cell membrane as an olfactory receptor, and is activated through binding with a smell molecule, and has a function to increase the intracellular cAMP level through conjugation with the intracellular Gαs on being activated followed by resulting activation of adenylate cyclase (Nat. Neurosci., 2004, 5:263-278).

In the present specification, the identity of a nucleotide sequence and amino acid sequence is calculated by using a Lipman-Pearson method (Science, 1985, 227:1435-41). Specifically, calculation is performed by using a homology analysis (Search homology) program of the genetic information processing software Genetyx-Win (ver. 5.1.1; Software Development Co.) with "Unit size to compare (ktup)" set at 2.

In the present specification, the term "an identity of at least 80%" with respect to a nucleotide sequence and amino acid sequence refers to an identity of 80% or higher, preferably 85% or higher, more preferably 90% or higher, further preferably 95% or higher, furthermore preferably 98% or higher, still furthermore preferably 99% or higher.

In the present specification, "sulfide compounds" refer to compounds represented by the following formula (I):

$$R^1-[S]_n-R^2 \qquad (I)$$

In the formula (I), $R^1$ and $R^2$ are the same or different, and each denote a linear-chain or branched-chain alkyl or alkenyl group having from 1 to 6 carbon atoms. Examples of the linear-chain or branched-chain alkyl group having from 1 to 6 carbon atoms include methyl, ethyl, propyl, isopropyl, butyl, isobutyl, sec-butyl, tert-butyl, pentyl, isopentyl, tert-pentyl, and hexyl. Examples of the linear-chain or branched-chain alkenyl group having from 1 to 6 carbon atoms include vinyl, propenyl, allyl, butenyl, and methylbutenyl. Preferably, the $R^1$ and $R^2$ are the same or different, and are each a linear-chain or branched-chain alkyl or alkenyl group having from 1 to 4 carbon atoms. Examples of the linear-chain or branched-chain alkyl or alkenyl group having from 1 to 4 carbon atoms include methyl, ethyl, propyl, isopropyl, butyl, isobutyl, sec-butyl, tert-butyl, vinyl, propenyl, allyl, and butenyl. More preferably, the $R^1$ and $R^2$ are the same or different, and are each methyl, ethyl, propyl, or isopropyl. Still more preferably, the $R^1$ and $R^2$ are each methyl.

In the formula (I), n denotes an integer of from 1 to 5, preferably an integer of from 1 to 3, and more preferably 2 or 3.

The "sulfide compound" is preferably a volatile substance having the structure represented by the formula (I). More preferred examples of the "sulfide compound" include dimethyl sulfide (DMS), dimethyl disulfide (DMDS), dimethyl trisulfide (DMTS), allylmethyl sulfide, and trimethyl sulfide. Further preferred examples are DMDS and DMTS.

"Odors of sulfide compounds" to be suppressed in the present invention are odors caused by the above-described "sulfide compounds", and preferably odors caused by DMDS or DMTS. Representatively, "odors of sulfide compounds" to be suppressed in the present invention may be malodors released from rotted kitchen garbage, sewage, or drain outlets.

As shown in FIGS. 1 and 2, the present inventors identified OR4S2 as an olfactory receptor specifically responsive to sulfide compounds from a number of olfactory receptors. OR4S2 responds to various sulfide compounds in a concentration-dependent manner. Accordingly, a substance which suppresses the response of OR4S2 or a polypeptide having a function comparable to OR4S2 changes recognition of odors of sulfide compounds on the basis of the olfactory receptor antagonism, and as a result odors of sulfide compounds can be selectively suppressed.

Thus, the present invention provides a method for evaluating and/or selecting an agent for suppressing odors of sulfide compounds. The method includes: adding a test substance and a sulfide compound to at least one olfactory receptor polypeptide selected from the group consisting of OR4S2 and polypeptides having an amino acid sequence identity of at least 80% to OR4S2; and measuring the response of the olfactory receptor polypeptide to the sulfide compound. On the basis of the response measured, a test substance which suppresses the response of the olfactory receptor polypeptide is identified. The test substance identified is selected as an agent for suppressing odors of sulfide compounds.

The method according to the present invention may be a method to be performed in vitro or ex vivo. In the method according to the present invention, a test substance and the sulfide compound are added to an olfactory receptor polypeptide having the responsiveness to the sulfide compound.

The test substance to be used in the method according to the present invention may be any substance intended to be used as an agent for suppressing odors of sulfide compounds, without any limitation. The test substance may be a naturally occurring substance, or a substance artificially synthesized through a chemical or biological method, etc., or a compound, or a composition or a mixture.

The olfactory receptor polypeptide to be used in the method according to the present invention is at least one selected from the group consisting of OR4S2 and polypeptides having an amino acid sequence identity of at least 80% to OR4S2.

OR4S2 is an olfactory receptor expressed in human olfactory cells. OR4S2 is registered in GenBank as GI: 116517324. OR4S2 is a protein consisting of the amino acid sequence as set forth in SEQ ID NO: 2, the amino acid sequence encoded by a gene having the nucleotide sequence as set forth in SEQ ID NO: 1.

Example of polypeptides having an amino acid sequence identity of at least 80% to OR4S2 include polypeptides consisting of an amino acid sequence having an identity of at least 80%, for example, 80% or higher, preferably 85% or higher, more preferably 90% or higher, further preferably 95% or higher, furthermore preferably 98% or higher, still furthermore preferably 99% or higher to the amino acid sequence as set forth in SEQ ID NO: 2, and having the responsiveness to the sulfide compounds.

Although the olfactory receptor polypeptide to be used in the method according to the present invention is only required to be at least one selected from the group consisting of the above-described olfactory receptor polypeptides, it may be a combination of two or more thereof. Preferably, OR4S2 is used.

In the method according to the present invention, the olfactory receptor polypeptide can be used in any form as long as it does not lose the responsiveness to the sulfide compounds. For example, the olfactory receptor polypeptide can be used in a form of a tissue or cell naturally expressing the olfactory receptor polypeptide such as the olfactory epithelium and olfactory sensory neuron isolated from the living body, or a culture thereof; a membrane of an olfactory cell carrying the olfactory receptor polypeptide; a recombinant cell genetically engineered to express the olfactory receptor polypeptide, or a culture thereof; a membrane of the recombinant cell having the olfactory receptor polypeptide; or an artificial lipid bilayer having the olfactory receptor polypeptide. All of these forms are included in the scope of the olfactory receptor polypeptide to be used in the present invention.

In a preferred aspect, the olfactory receptor polypeptide can be a cell naturally expressing the olfactory receptor polypeptide such as an olfactory cell of a mammal, or a recombinant cell genetically engineered to express the olfactory receptor polypeptide, or a culture thereof. Preferred examples include a recombinant human cell genetically engineered to express the olfactory receptor polypeptide. The recombinant cell can be produced through transformation of a cell with a vector in which a gene encoding the olfactory receptor polypeptide has been incorporated.

To promote the expression of the olfactory receptor polypeptide on a cell membrane, a gene encoding RTP (receptor-transporting protein) is suitably introduced into a cell together with a gene encoding the olfactory receptor polypeptide. Preferably, a gene encoding a short form of RTP1 (RTP1S) is introduced into a cell together with a gene encoding the olfactory receptor polypeptide. Examples of RTP1S include human RTP1S. The human RTP1S is a protein registered in GenBank as GI: 50234917 and consisting of the amino acid sequence as set forth in SEQ ID NO: 4, the amino acid sequence encoded by a gene having the nucleotide sequence as set forth in SEQ ID NO: 3.

According to the method of the present invention, addition of a test substance and the sulfide compound to the olfactory receptor polypeptide is followed by measurement of the response of the olfactory receptor polypeptide to the sulfide compound. The measurement can be performed by using any method known in the art as a method for measuring the response of an olfactory receptor such as intracellular cAMP level measurement. For example, olfactory receptors are known to increase the intracellular cAMP level through conjugation with the intracellular Gαs on being activated by a smell molecule followed by resulting activation of adenylate cyclase (Nat. Neurosci., 2004, 5:263-278). Accordingly, the response of the olfactory receptor polypeptide can be measured by using, as an indicator, the intracellular cAMP level after addition of a smell molecule. Examples of methods for measuring the cAMP level include ELISA and reporter gene assay. Another method for measuring the response of the olfactory receptor polypeptide is, for example, calcium imaging. Still another method is, for example, electrophysiological measurement. In electrophysiological measurement, for example, a cell (e.g., an oocyte of an *Xenopus laevis*) co-expressing the olfactory receptor polypeptide and an additional ion channel is produced, and the response of the olfactory receptor polypeptide is measured through measurement of the activity of the ion channel on the cell by using a patch-clamp method, a two-electrode voltage-clamp method, or the like.

Further, the test substance which suppresses the response can be identified through evaluation of the action of the test substance on the response to the sulfide compound on the basis of the response of the olfactory receptor polypeptide measured. Evaluation of the action of the test substance can be performed through comparison between the response of the olfactory receptor polypeptide with the test substance to the sulfide compound and the response to the sulfide compound for a control group. Examples of the control group include the olfactory receptor polypeptide to which the test substance at a different concentration is added, the olfactory receptor polypeptide to which the test substance is not added, the olfactory receptor polypeptide to which control substance is added, the olfactory receptor polypeptide before addition of the test substance, and a cell not expressing the olfactory receptor polypeptide.

The action of the test substance on the response of the olfactory receptor polypeptide can be evaluated, for example, through comparison of the response of the olfactory receptor polypeptide to the sulfide compound between a group with the test substance at a higher concentration and a group with the test substance at a lower concentration, between a group with the test substance and a group without the test substance, between a group with the test substance and a group with a control substance, or between before and after addition of the test substance. When the response of the olfactory receptor polypeptide is suppressed by addition of the test substance or addition of the test substance at a higher concentration, the test substance can be then identified as a substance which suppresses the response of the olfactory receptor polypeptide to the sulfide compound.

When the response for a group with the test substance is suppressed in comparison with that for a control group, the test substance can be then identified as a substance which suppresses the response of the olfactory receptor polypeptide to the sulfide compound. For example, when the response of the olfactory receptor polypeptide measured for a group with the test substance in the above procedure is suppressed to preferably 60% or less, more preferably 50% or less, further preferably 25% or less of that for a control group, the test substance can be then identified as a substance which suppresses the response of the olfactory receptor polypeptide to the sulfide compound. Or, when the response of the olfactory receptor polypeptide measured for a group with the test substance in the above procedure is statistically significantly suppressed in comparison with that for a control group, the test substance can be then identified as a substance which suppresses the response of the olfactory receptor polypeptide to the sulfide compound.

The test substance identified in the above procedure is a substance capable of suppressing recognition of the odor of the sulfide compound by an individual through suppression of the response of the olfactory receptor to the sulfide compound. Thus, the test substance identified in the above procedure can be selected as an agent for suppressing odors of sulfide compounds. The substance selected as an agent for suppressing odors of sulfide compounds through the method according to the present invention can suppress the odor of the sulfide compound through suppression of the response of the olfactory receptor to the sulfide compound.

Accordingly, in one embodiment, the substance selected through the method according to the present invention can be an active ingredient of an agent for suppressing odors of sulfide compounds. Alternatively, the substance selected through the method according to the present invention can be contained in a compound or composition for suppressing odors of sulfide compounds as an active ingredient for suppressing odors of sulfide compounds. Further alternatively, the substance selected through the method according to the present invention can be used for production of an agent for suppressing odors of sulfide compounds, or for production of a compound or composition for suppressing odors of sulfide compounds.

As exemplary embodiments of the present invention, the following substances, production methods, applications, and methods are disclosed herein. However, the present invention is never limited to these embodiments.

[1] A method for evaluating and/or selecting an agent for suppressing odors of sulfide compounds, the method comprising:
adding a test substance and a sulfide compound to at least one olfactory receptor polypeptide selected from the group consisting of OR4S2 and polypeptides having an amino acid sequence identity of at least 80% to OR4S2; and
measuring the response of the olfactory receptor polypeptide to the sulfide compound.

[2] The method according to [1], wherein the sulfide compound is preferably a compound represented by the following formula (I):

$$R^1-[S]_n-R^2 \qquad (I)$$

wherein $R^1$ and $R^2$ are the same or different, and each denote a linear-chain or branched-chain alkyl or alkenyl group having from 1 to 6 carbon atoms, and n denotes an integer of from 1 to 5.

[3] The method according to [2], wherein,
preferably, the $R^1$ and $R^2$ are the same or different, and are each a linear-chain or branched-chain alkyl or alkenyl group having from 1 to 4 carbon atoms,
more preferably, the $R^1$ and $R^2$ are the same or different, and are each methyl, ethyl, propyl, or isopropyl, and
further preferably, the $R^1$ and $R^2$ are each methyl.

[4] The method according to [2] or [3], wherein the n is preferably an integer of from 1 to 3, and more preferably 2 or 3.

[5] The method according to any one of [1] to [4], wherein the sulfide compound is preferably dimethyl sulfide, dimethyl disulfide, or dimethyl trisulfide.

[6] The method according to any one of [1] to [5], wherein the odor of the sulfide compound is preferably malodor released from rotted kitchen garbage, sewage, or drain outlets.

[7] The method according to any one of [1] to [6], wherein the OR4S2 is preferably a protein consisting of the amino acid sequence as set forth in SEQ ID NO: 2.

[8] The method according to any one of [1] to [7], wherein the polypeptide having an amino acid sequence identity of at least 80% to OR4S2 is preferably a polypeptide consisting of an amino acid sequence having an identity of preferably 80% or higher, more preferably 85% or higher, further preferably 90% or higher, even further preferably 95% or higher, furthermore preferably 98% or higher, still furthermore preferably 99% or higher to the amino acid sequence as set forth in SEQ ID NO: 2, and having the responsiveness to the sulfide compound.

[9] The method according to any one of [1] to [8], preferably further comprising identifying a test substance which suppresses the response of the olfactory receptor polypeptide on the basis of the response measured.

[10] The method according to any one of the above [1] to [8], preferably further comprising:
measuring the response to the sulfide compound for a control group, wherein
the control group is any one of the following:
the olfactory receptor polypeptide to which the test substance is not added;
the olfactory receptor polypeptide to which a control substance is added;
the olfactory receptor polypeptide before addition of the test substance; and
a cell not expressing the olfactory receptor polypeptide.

[11] The method according to the above [10], preferably further comprising:
identifying the test substance as a substance which suppresses the response of the olfactory receptor polypeptide to the sulfide compound, when the response of the olfactory receptor polypeptide to which the test substance is added to the sulfide compound is statistically significantly suppressed in comparison with that for the control group.

[12] The method according to the above [10], preferably further comprising:
identifying the test substance as a substance which suppresses the response of the olfactory receptor polypeptide to the sulfide compound, when the response of the olfactory receptor polypeptide to which the test substance is added to the sulfide compound is suppressed to preferably 60% or less, more preferably 50% or less, further preferably 25% or less of that for the control group.

[13] The method according to any one of [1] to [12], preferably further comprising selecting the test substance which suppresses the response of the olfactory receptor polypeptide to the sulfide compound as an agent for suppressing odors of sulfide compounds.

[14] The method according to any one of [1] to [13], wherein the at least one olfactory receptor polypeptide selected from the group consisting of OR4S2 and polypeptides having an amino acid sequence identity of at least 80% to OR4S2 is preferably expressed on a recombinant cell genetically engineered to express the olfactory receptor polypeptide.

[15] The method according to the above [14], wherein the recombinant cell is
preferably, a cell into which a gene encoding the olfactory receptor polypeptide and a gene encoding RTP1S have been introduced, and
more preferably, a cell into which a gene encoding the olfactory receptor polypeptide and a gene encoding human RTP1S have been introduced.

[16] The method according to any one of [1] to [13], wherein the recombinant cell set forth in the above [14] or [15] or a culture thereof is preferably used as the at least one olfactory receptor polypeptide selected from the group consisting of OR4S2 and polypeptides having an amino acid sequence identity of at least 80% to OR4S2.

[17] The method according to any one of [1] to [16], wherein the measurement of the response of the olfactory receptor polypeptide is preferably intracellular cAMP level measurement with ELISA or reporter gene assay, measurement with calcium imaging, or electrophysiological measurement.

EXAMPLES

Hereinafter, the present invention will be more specifically described with reference to Examples.

Odor compounds and test substances used in Examples are listed in the following Table 1.

TABLE 1

|  | Cas No. | Name of provider |
|---|---|---|
| Sulfide compound |  |  |
| Dimethyl disulfide (DMDS) | 624-92-0 | SIGMA-ALDRICH CO., LCC. |
| Dimethyl trisulfide (DMTS) | 3658-80-8 | SIGMA-ALDRICH CO., LCC. |
| Dimethylsulfide (DMS) | 75-18-3 | Wako Pure Chemical Industries, Ltd. |
| Sulfur compound |  |  |
| Methylmercaptan | 5188-07-8 | Tokyo Chemical Industry Co., Ltd. |
| Test substance |  |  |
| Cis-4-Heptenal (or (Z)-Hept-4-enal) | 6728-31-0 | SIGMA-ALDRICH CO., LCC. |
| 1,4-Cineole | 470-67-7 | SIGMA-ALDRICH CO., LCC. |

Example 1: Identification of Olfactory Receptor Responsive to Sulfide Compound (1) Cloning of Human Olfactory Receptor Gene A human olfactory receptor was cloned by using the PCR method with human genomic DNA female (G1521: Promega Corporation) as a template on the basis of sequence information registered in GenBank. Each gene amplified through the PCR method was incorporated into a pENTR vector (Invitrogen) in accordance with the manual, and recombined, by utilizing the NotI and AscI sites present in the pENTR vector, with a pME18S vector at the NotI and AscI sites produced in the downstream of the Flag-Rho tag sequence of the pME18S vector.

(2) Preparation of pME18S-Human RTP1S Vector

An RTP1S gene (SEQ ID NO: 3) encoding RTP1S (SEQ ID NO: 4) was incorporated into the pME18S vector at the EcoRI and XhoI sites thereof.

(3) Preparation of Olfactory Receptor-Expressing Cells

HEK293 cells expressing any one of 428 human olfactory receptors were produced. A reaction solution with a composition shown in Table 2 was prepared and left to stand in a clean bench for 15 minutes, and then added to each well of a 96-well plate (BD Biosciences). Subsequently, 90 μL of HEK293 cells ($3 \times 10^5$ cells/cm$^2$) was seeded in each well, and cultured in an incubator retained at 37° C. and 5% $CO_2$ for 24 hours. As a control, cells with conditions for no expression of an olfactory receptor (Mock) were prepared and used in an experiment.

TABLE 2

| DMEM (Nacalai) | 10 μL |
|---|---|
| human olfactory receptor gene (incorporated in pME18S vector with addition of Flag-Rho tag at N-terminal) | 0.075 μg |
| pGL4.29 (fluc2P-CRE-hygro, Promega Corporation) | 0.03 μg |
| pGL4.75 (hRluc-CMV, Promega Corporation) | 0.03 μg |
| pME18S-human RTP1S vector | 0.03 μg |
| lipofectamine 2000 (Invitrogen) | 0.4 μL |

(4) Luciferase Assay

An olfactory receptor expressed on HEK293 cells increases the intracellular cAMP level through conjugation with the intracellular Gαs followed by resulting activation of adenylate cyclase. For smell response measurement in this study, luciferase reporter gene assay was used in which increase of the intracellular cAMP level is monitored as an emission value derived from a firefly luciferase gene (fluc2P-CRE-hygro). Transgenesis was simultaneously performed by using a product with a sea pansy luciferase gene fused to the downstream of the CMV promoter (hRluc-CMV), and the resultant was used as an internal standard to correct errors of transgenesis efficiency and the number of cells.

The medium was removed from the culture prepared in the above (3), and 75 μL of a solution containing a sulfide compound prepared with DMEM (NACALAI TESQUE, INC.) was added. The sulfide compound was 100 μM of dimethyl disulfide (DMDS) or dimethyl trisulfide (DMTS). The cells were cultured in a $CO_2$ incubator for 3 hours to allow the luciferase gene to be sufficiently expressed in the cells. Measurement of the activity of luciferase was performed by using a Dual-Glo™ luciferase assay system (Promega Corporation) in accordance with an operation manual of the product. For each stimulus condition, the value fLuc/hRluc was calculated by dividing the emission value derived from firefly luciferase by the emission value derived from sea pansy luciferase. The value fLuc/hRluc derived from firefly luciferase and induced by a stimulus of a sulfide compound was divided by the value fLuc/hRluc for cells without a stimulus of a sulfide compound to calculate a fold increase, and the fold increase was used as an indicator of intensity of response.

(5) Results

The response to DMDS or DMTS was measured for 428 olfactory receptors, and the results revealed that the olfactory receptor OR4S2 exhibits a specific response to both of DMDS and DMTS (FIG. 1). The response of OR4S2 to DMDS and DMTS was in a concentration-dependent manner (FIG. 2). In addition, OR4S2 responded to dimethyl sulfide (DMS) at a concentration of 1 mM and 3 mM (FIG. 3). On the other hand, OR4S2 did not respond to 3 mM of methylmercaptan (FIG. 4), which is also a volatile sulfur compound. Therefore, OR4S2 is a sulfide compound receptor responsive to various sulfide compounds. Further, OR4S2 is a novel sulfide compound receptor which has not been found to respond to sulfide compounds.

Example 2: Searching for Agent for Suppressing Odors of Sulfide Compounds on the Basis of Response of Olfactory Receptor (1) Luciferase Assay By using the same procedure as in Example 1 (1) to (3), HEK293 cells expressing OR4S2 (SEQ ID NO: 2) were prepared. The response of the olfactory receptor to DMDS (the value fLuc/hRluc) was measured in the presence and absence of a test substance by using luciferase reporter gene assay in accordance with the procedure in Example 1 (4). The value fLuc/hRluc induced by a stimulus of single DMDS, (X), the value fLuc/hRluc for cells without a stimulus of DMDS, (Y), and the value fLuc/hRluc induced by a co-stimulus of DMDS and a test substance, (Z), were determined, and the intensity of the response (Response (%)) of the receptor to DMDS in the presence of a test substance was determined by using the following formula.

Response (%)=(Z−Y)/(X−Y)×100

The experiment was performed independently three times, and the average value of the experiments was determined. The concentration of DMDS to be added to a culture was set at 1 mM, and the concentration of a test substance to be added was changed in the range of from 0 to 3000 µM.

For the response to DMTS, the value fLuc/hRluc to a stimulus of single DMTS, (X'), was divided by the value fLuc/hRluc for cells without a stimulus of DMTS, (Y), and the value obtained by the division, (X'/Y), was set as a value of the response to DMTS (Fold increase). To compare the effect of a test substance on the response to DMTS, the value fLuc/hRluc induced by a co-stimulus of DMTS and a test substance, (Z'), was similarly divided by the value fLuc/hRluc for cells without a stimulus, (Y), to calculate (Z'/Y) as Fold increase. The experiment was performed independently three times, and the average value of the experiments was determined. The concentration of DMTS to be added to a culture was set at 300 µM, and the concentration of a test substance to be added was set at 100 µM.

The results are shown in FIGS. 5 and 6. cis-4-Heptenal and 1,4-cineol both suppressed the response of OR4S2 to DMDS in a concentration-dependent manner. In addition, the two compounds both suppressed the response of OR4S2 to DMTS. These results revealed that the two compounds are each an OR4S2 antagonist.

Example 3: Ability of OR4S2 Antagonists to Suppress Odors of Sulfide Compounds

The odor-suppressing effect of each of cis-4-heptenal and 1,4-cineol, as the OR4S2 antagonists identified in Example 2, for sulfide compounds was checked in a sensory test.

For each of DMDS, cis-4-heptenal, and 1,4-cineol, a 0.1% (v/v) solution in mineral oil was prepared. For DMTS, a 0.01% (v/v) solution in mineral oil was prepared. Two cotton balls were put in a 20 mL glass bottle (Maruemu Corporation, No. 6), and one cotton ball was impregnated with 30 µL of the DMDS or DMTS solution, and the other cotton ball was impregnated with 30 µL a solution of one of the OR4S2 antagonists. The glass bottle containing the cotton balls was covered with a lid, and left to stand at 37° C. for 1 hour, and thereafter used as a test sample for a sensory test. Glass bottles containing only a cotton ball impregnated with the DMDS or DMTS solution were prepared as reference samples, and a glass bottle containing only a cotton ball impregnated with mineral oil (Vehicle) was prepared as a control sample.

A sensory test was performed in a single-blinded mode with 10 evaluators for DMDS and 11 evaluators for DMTS. The test was initiated after two o'clock pm, which was 1.5 hours or longer after a meal. To prevent diffusion of a smell, the test was performed essentially under a fume hood. To eliminate the influence of adaptation to odors of sulfide compounds, the evaluators were appropriately checked for the intensity of recognition to the odor of DMDS or DMTS in the test, and rested as necessary. The evaluators were separated into two groups, and one group evaluated the odor-suppressing effect for DMDS or DMTS with respect to cis-4-heptenal and 1,4-cineol, in the order presented, and the other group evaluated it with respect to 1,4-cineol and cis-4-heptenal, in the order presented. Each test sample was replaced with another one after evaluation by each of three evaluators.

In evaluation of odors of test samples, the following criteria in five grades were set for each evaluator: "odor of DMDS (or DMTS) was 1: unidentifiable, 2: perceivable, 3: easily identifiable, 4: strong, 5: intolerably strong", and the evaluators rated the odor intensity of DMDS (or DMTS) for each test sample in nine grades from 1.0 to 5.0 at an interval of 0.5, where the odor intensity of single DMDS (or DMTS) was assumed as 3. The average value of the evaluation results by the evaluators was determined.

The results of the sensory test are shown in FIG. 7. cis-4-Heptenal and 1,4-cineol, each as an OR4S2 antagonist, both suppressed the odor intensity of DMDS and DMTS. The above-described results revealed that the OR4S2 antagonists suppress odors of sulfide compounds including DMDS and DMTS, and thus an agent for suppressing odors of sulfide compounds can be searched on the basis of the response of OR4S2 in an efficient manner.

The invention claimed is:

1. A method for evaluating and/or selecting an agent for suppressing odors of sulfide compounds, the method comprising:
    adding a test substance and a sulfide compound to a cell expressing an olfactory receptor polypeptide, wherein the olfactory receptor polypeptide is at least one selected from the group consisting of (i) a polypeptide comprising the amino acid sequence of SEQ ID NO: 2, and (ii) a polypeptide having an amino acid sequence identity of at least 95% to SEQ ID NO: 2;
    measuring the response of the olfactory receptor polypeptide to the sulfide compound;
    measuring the response of the olfactory receptor polypeptide to which the test substance is not added to the sulfide compound; and,
    identifying the test substance as a substance which suppresses the response of the olfactory receptor polypeptide to the sulfide compound, when the response of the olfactory receptor polypeptide to which the test substance is added to the sulfide compound is more suppressed than the response of the olfactory receptor polypeptide to which the test substance is not added to the sulfide compound.

2. The method according to claim 1, wherein the sulfide compound is a compound represented by formula (I):

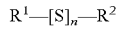

$$R^1-[S]_n-R^2 \quad (I)$$

wherein $R^1$ and $R^2$ are the same or different, and each denote a linear-chain or branched-chain alkyl or alkenyl group having from 1 to 6 carbon atoms, and n denotes an integer of from 1 to 5.

3. The method according to claim 2, wherein the $R^1$ and $R^2$ are the same or different, and are each a linear-chain or branched-chain alkyl or alkenyl group having 1 to 4 carbon atoms, and n is an integer of 1 to 3.

4. The method according to claim 1, wherein the olfactory receptor polypeptide comprises the amino acid sequence of SEQ ID NO: 2.

5. The method according to claim 1, wherein the olfactory receptor polypeptide is expressed on a recombinant cell genetically engineered to express the olfactory receptor polypeptide.

6. The method according to claim 1, wherein the measurement of the response of the olfactory receptor polypeptide is intracellular cAMP level measurement with ELISA or reporter gene assay, measurement with calcium imaging, or electrophysiological measurement.

7. The method according to claim 1, wherein the olfactory receptor polypeptide has an amino acid sequence identity of at least 98% to SEQ ID NO: 2.

8. The method according to claim 1, wherein the olfactory receptor polypeptide has an amino acid sequence identity of at least 99% to SEQ ID NO: 2.

* * * * *